United States Patent [19]
Balko

[11] 4,195,092
[45] Mar. 25, 1980

[54] 2-(SUBSTITUTED AMINO)-N-(3-SUBSTITUTED PHENYL)-2-IMIDAZOLINE-1-CARBOTHIOAMIDES

[75] Inventor: Terry W. Balko, Waldron, Ind.

[73] Assignee: Eli Lilly and Company, Indianapolis, Ind.

[21] Appl. No.: 865,091

[22] Filed: Dec. 27, 1977

[51] Int. Cl.$^2$ .................. A61K 31/415; C07D 233/50
[52] U.S. Cl. .................. 424/273 R; 548/315; 548/316; 544/139; 546/210; 546/278; 424/248.5; 424/250; 424/263; 424/267
[58] Field of Search .................. 548/315; 424/273 R

[56]  References Cited
U.S. PATENT DOCUMENTS

| | | | |
|---|---|---|---|
| 3,459,763 | 8/1969 | Greenfeld | 548/315 |
| 3,887,552 | 6/1975 | Stähle et al. | 548/315 |
| 3,979,408 | 9/1976 | Trani | 548/315 |
| 4,080,503 | 3/1978 | Kummer et al. | 548/315 |

FOREIGN PATENT DOCUMENTS

| | | | |
|---|---|---|---|
| 741948 | 11/1969 | Belgium | 548/315 |
| 770136 | 10/1967 | Canada | 548/315 |
| 66/7833 | 5/1967 | South Africa | 548/315 |
| 1157632 | 7/1969 | United Kingdom | 548/315 |

Primary Examiner—Alan L. Rotman
Assistant Examiner—Natalia Harkaway
Attorney, Agent, or Firm—Leroy Whitaker; Arthur R. Whale

[57] ABSTRACT

2-(Substituted amino)-N-(3-substituted phenyl)-2-imidazoline-1-carbothioamides, useful as insecticides.

89 Claims, No Drawings

2-(SUBSTITUTED AMINO)-N-(3-SUBSTITUTED PHENYL)-2-IMIDAZOLINE-1-CARBOTHIOAMIDES

BACKGROUND OF THE INVENTION

This invention relates to 2-imidazolines. More particularly, this invention relates to 2-(substituted amino)-N-(3-substituted phenyl)-2-imidazoline-1-carbothioamides which are useful as insecticides.

British Patent Specification No. 1,157,632 and Canadian Pat. No. 770,136 disclose N-(phenyl or substituted phenyl)-2-thioxoimidazolidine-1-carbothioamides, useful as anorexics and antidepressants. Also disclosed are N-(phenyl or substituted phenyl)-2-alkylthio-2-imidazoline-1-carbothioamides which are useful as intermediates to the claimed compounds. The latter class of compounds is discussed by C. Di Bello et al., Gazz. Chim. Ital., 100, 86 (1970) [Chem. Abstr., 72, 132627f (1970)].

South African Pat. No. 66/7833 discloses N,N-dialkyl-2-thioxoimidazolidine-1-carbothioamides which are useful as anorexic agents.

The principal compounds of the above-described references are prepared by the reaction of ethylene diisothiocyanate with an amine. This reaction is discussed by F. D'Angeli et al., J. Org. Chem., 28, 1596 (1963).

Belgian Pat. No. 741,948 generically discloses N-substituted and N,N-disubstituted 1-carbamoyl- and 1-thiocarbamoyl-2-phenylamino-2-imidazolines. The reference, however, clearly is directed primarily to the 1-carbamoyl compounds.

Finally, W. Reid et al., Chem. Ber., 106, 484 (1973), disclose 2,N-diphenyl-2-imidazoline-1-carbothioamide.

SUMMARY OF THE INVENTION

In accordance with the present invention, 2-(substituted amino)-N-(3-substituted phenyl)-2-imidazoline-1-carbothioamides are provided having the formula,

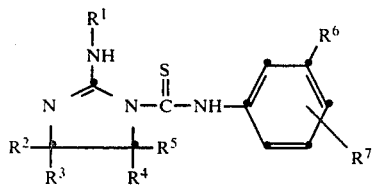

wherein $R^1$ represents
(A) $C_1$-$C_{18}$ alkyl;
(B) $C_2$-$C_{18}$ alkenyl;
(C) $C_4$-$C_{18}$ alkadienyl;
(D) $C_3$-$C_{12}$ cycloalkyl, optionally substituted with either one or two $C_1$-$C_3$ alkyl groups;
(E) $C_5$-$C_{12}$ cycloalkenyl, optionally substituted with either one or two $C_1$-$C_3$ alkyl groups;
(F) $C_6$-$C_{12}$ cycloalkadienyl, optionally substituted with either one or two $C_1$-$C_3$ alkyl groups;
(G) phenyl, optionally substituted with from one to three groups selected from the group consisting of
 (1) $C_1$-$C_6$ alkyl,
 (2) $C_1$-$C_6$ alkoxy,
 (3) $C_1$-$C_6$ alkylthio,
 (4) trifluoromethyl,
 (5) halo, and
 (6) cyano;
(H) (cycloalkyl)alkyl, containing no more than about 18 carbon atoms, in which the cycloalkyl moiety is as defined hereinabove;
(I) phenylalkyl, containing no more than about 18 carbon atoms, in which the phenyl moiety is as defined hereinabove;
(J) diphenylalkyl, containing no more than about 18 carbon atoms, in which each phenyl moiety is as defined hereinabove;
(K) pyridyl, optionally substituted with either one or two groups selected from the group consisting of
 (1) $C_1$-$C_3$ alkyl,
 (2) $C_1$-$C_3$ alkoxy, or
 (3) halo;
(L) piperidino, optionally substituted with either one or two $C_1$-$C_3$ alkyl groups;
(M) morpholino;
(N) pyrazinyl, optionally substituted with either one or two $C_1$-$C_3$ alkyl groups;
(O) pyridylalkyl, containing no more than about 17 carbon atoms, in which the pyridyl moiety is as defined hereinabove;
(P) piperidinoalkyl, containing no more than about 17 carbon atoms, in which the piperidino moiety is as defined hereinabove;
(Q) morpholinoalkyl, containing no more than about 16 carbon atoms;
(R) pyrazinylalkyl, containing no more than about 16 carbon atoms, in which the pyrazinyl moiety is as defined hereinabove;
(S) tetrahydrofurylalkyl, containing no more than about 17 carbon atoms; and
(T) substituted amino having the formula,

in which $R^8$ and $R^9$ independently are selected from the group consisting of hydrogen, $C_1$-$C_{18}$ alkyl, phenyl, and phenylalkyl wherein the phenyl and phenylalkyl moieties are as defined hereinabove, provided that at least one of $R^8$ and $R^9$ is other than hydrogen;

$R^2$ and $R^3$ independently are selected from the group consisting of
(A) hydrogen,
(B) $C_1$-$C_3$ alkyl, and
(C) phenyl, with the proviso that when one of $R^2$ and $R^3$ is phenyl, the other of $R^2$ and $R^3$ is hydrogen;

$R^4$ and $R^5$ independently are selected from the group consisting of
(A) hydrogen,
(B) $C_1$-$C_3$ alkyl, and
(C) phenyl, with the proviso that when one of $R^4$ and $R^5$ is phenyl, the other of $R^4$ and $R^5$ is hydrogen;

$R^6$ represents
(A) halo,
(B) trifluoromethyl,
(C) cyano, or
(D) 1,1,2,2-tetrafluoroethoxy;

$R^7$ represents hydrogen, $C_1$-$C_3$ alkyl, or halo, with the proviso that $R^7$ can not be in the 2-position.

A preferred group of compounds comprises the compounds of the above formula wherein each of $R^2$, $R^3$, $R^4$, and $R^5$ is hydrogen.

A more preferred group of compounds comprises the compounds of the above formula wherein
$R^1$ represents
(1) alkyl,
(2) phenyl, optionally monosubstituted with $C_1$–$C_3$ alkyl, $C_1$–$C_3$ alkoxy, trifluoromethyl, or halo, or optionally disubstituted with halo,
(3) phenylalkyl, in which the phenyl moiety is unsubstituted, or
(4) 2-pyridylalkyl;
each of $R^2$, $R^3$, $R^4$, and $R^5$ is hydrogen;
$R^6$ is selected from the group consisting of chloro, bromo, trifluoromethyl, and cyano; and
$R^7$ is hydrogen.

A most preferred group of compounds comprises the compounds of the above formula wherein
$R^1$ represents
(1) $C_1$–$C_6$ alkyl,
(2) phenyl, optionally monosubstituted with fluoro, chloro, or bromo, or optionally disubstituted with chloro,
(3) $C_7$–$C_{10}$ phenylalkyl, in which the phenyl moiety is unsubstituted, or
(4) 2-pyridylalkyl, containing no more than about 7 carbon atoms, in which the pyridyl moiety is unsubstituted; and
$R^2$–$R^7$, inclusive, are as defined for the above-described preferred group of compounds.

The present invention also provides a method for reducing or eradicating a population of the insect species *Epilachna varivestis* which comprises administering to the insect by ingestion an insecticidally-effective amount of a compound of the above formula.

Additionally, the present invention provides an insecticidal composition which comprises an insecticidally-effective amount of a compound of the above formula and an agriculturally-acceptable carrier.

DETAILED DESCRIPTION OF THE INVENTION

In the above formula, the various chemical groups have their usual meanings. For the sake of clarity, however, examples of the various generally-named groups will be given.

The term "$C_1$–$C_{18}$ alkyl" includes, among others, methyl, ethyl, propyl, isopropyl, butyl, isobutyl, pentyl, neopentyl, 1-methylbutyl, hexyl, isohexyl, 2,3-dimethylbutyl, 1-ethylpentyl, 2-ethyl-3-methylbutyl, 2-ethylhexyl, 6-methylheptyl, nonyl, 2,4,4-trimethylhexyl, decyl, 7,7-dimethyloctyl, 1-propylheptyl, 1,1-dimethyloctyl, undecyl, 3-ethyl-2,6-dimethylheptyl, 10-methylundecyl, 5-ethyl-2,6-dimethyloctyl, tridecyl, 2,2,6,6,7-pentamethyloctyl, 9-ethyldodecyl, pentadecyl, 5-sec-butyl-2,7-dimethylnonyl, 14-methylpentadecyl, 3-propyl-8-ethyldodecyl, octadecyl, 1-methylheptadecyl, and the like.

The terms "$C_2$–$C_{18}$ alkenyl" and "$C_4$–$C_{18}$ alkadienyl" include, among others, vinyl, 1-propenyl, allyl, isopropenyl, 1-butenyl, 2-butenyl, 1-pentenyl, 2-pentenyl, 2-methyl-2-butenyl, 1-hexenyl, 2-hexenyl, 3-hexenyl, 4-methyl-1-pentenyl, 2-methyl-1pentenyl, 2-methyl-2-pentenyl, 3-methyl-2-pentenyl, 2,3-dimethyl-2-butenyl, 3,3-dimethyl-1-butenyl, 1-heptenyl, 2-heptenyl, 4-methyl-1-hexenyl, 2,4-dimethyl-1-pentenyl, 2-propyl-1-butenyl, 2,3,3-trimethyl-1-butenyl, 1-octenyl, 2-octenyl, 4-octenyl, 2,4,4-trimethyl-1-pentenyl, 1-nonenyl, 2,3-diethyl-2-pentenyl, 1-decenyl, 5-decenyl, 3-isopropyl-3-heptenyl, 4-undecenyl, 1-dodecenyl, 2-methyl-1-undecenyl, 2,2,4,6,6-pentamethyl-3-heptenyl, 1-tridecenyl, 3-tetradecenyl, 5-pentadecenyl, 1-hexadecenyl, 1,5-dimethyl-2-ethyl-3-propyl-4-nonenyl, 1-octadecenyl, 1,3-butadienyl, 1,3-pentadienyl, 1,4-pentadienyl, 2-methyl-1,3-butadienyl, 3-methyl-1,2-butadienyl, 1,2-hexadienyl, 1,4-hexadienyl, 1,5-hexadienyl, 2,4-hexadienyl, 2-ethyl-1,3-butadienyl, 2-methyl-1,3-pentadienyl, 4-methyl-1,3-pentadienyl, 2,3-dimethyl-1,3-butadienyl, 1,4-heptadienyl, 1,6-heptadienyl, 2,4-dimethyl-1,3-pentadienyl, 1,7-octadienyl, 2,5-dimethyl-2,4-hexadienyl, 1,8-nonadienyl, 7-methyl-2,4-octadienyl, 1,3-decadienyl, 2,6-dimethyl-2,6-octadienyl, 1,10-undecadienyl, 5,6-dimethyl-4-ethyl-1,2-heptadienyl, 1,5-dodecadienyl, 1,12-tridecadienyl, 4-isopropyl-1,9-decadienyl, 6,8-tetradecadienyl, 6,9-pentadecadienyl, 1,15-hexadecadienyl, 6,10-hexadecadienyl, 2,3,11-trimethyl-6,9-tridecadienyl, 7,10-heptadecadienyl, 1,17-octadecadienyl, 2-methyl-7,10-heptadecadienyl, and the like.

The term "$C_1$–$C_3$ alkyl" includes methyl, ethyl, propyl, and isopropyl. Thus, the phrase "$C_3$–$C_{12}$ cycloalkyl optionally substituted with either one or two $C_1$–$C_3$ alkyl groups" is meant to include, among others, such groups as cyclopropyl, 2-ethylcyclopropyl, cyclobutyl, 2,3-dimethylcyclobutyl, cyclopentyl, 3-propylcyclopentyl, cyclohexyl, 2-methyl-4-isopropylcyclohexyl, cycloheptyl, 3-ethylcycloheptyl, cyclooctyl, cyclononyl, 3,5-diisopropylcyclononyl, cyclodecyl, 1-methyl-4-ethylcyclodecyl, cycloundecyl, cyclododecyl, and the like.

The phrases "$C_5$–$C_{12}$ cycloalkenyl, optionally substituted . . . " and "$C_6$–$C_{12}$ cycloalkadienyl, optionally substituted . . . " are meant to include, among others, such groups as cyclopentenyl, 2-ethylcyclopentenyl, cyclohexenyl, 4-methylcyclohexenyl, 2-isopropyl-5-methylcyclohexenyl, cycloheptenyl, cyclooctenyl, 3,5-dimethylcyclooctenyl, cyclononenyl, 2-ethylcyclononenyl, cyclodecenyl, 4-isopropyl-7-methylcyclodecenyl, cycloundecenyl, 5-methylcycloundecenyl, cyclododecenyl, 3-propylcyclododecenyl, 1,3-cyclohexadienyl, 5-methyl-1,3-cyclohexadienyl, 1,4-cyclohexadienyl, 1,3-cycloheptadienyl, 2,4-dimethyl-1,3-cycloheptadienyl, 2,4-cycloheptadienyl, 1,3-cyclooctadienyl, 1,4-cyclooctadienyl, 1,5-cyclooctadienyl, 1-methyl-2,5-cyclooctadienyl, 1,4-cyclononadienyl, 3,6-dipropyl-1,3-cyclononadienyl, 1,3-cyclodecadienyl, 3-ethyl-1,5-cyclodecadienyl, 2,6-cycloundecadienyl, 4-ethyl-5-methyl-1,7-cycloundecadienyl, 1,3-cyclododecadienyl, 1,7-cyclododecadienyl, 3-propyl-2,5-cyclododecadienyl, and the like.

The term "$C_1$–$C_6$ alkyl" and the alkyl moiety in the terms "$C_1$–$C_6$ alkylthio" and "$C_1$–$C_6$ alkoxy" include methyl, ethyl, propyl, isopropyl, butyl, isobutyl, sec-butyl, t-butyl, pentyl, isopentyl, 1-methylbutyl, 1-ethylpropyl, neopentyl, hexyl, isohexyl, and the like. Similarly, the phrase "phenyl, optionally substituted with . . . " is meant to include, among others, such groups as phenyl, m-tolyl, o-cumenyl, 4-hexylphenyl, 3-trifluoromethylphenyl, 3-isobutylthiophenyl, 2-ethoxyphenyl, 2-fluorophenyl, 3-chlorophenyl, 4-bromophenyl, 3-iodophenyl, 4-cyanophenyl, 2,6-xylyl, 2,4-bis(trifluoromethyl)phenyl, 2-methylthio-4-butylthiophenyl, 2,3-dimethoxyphenyl, 3,5-dichlorophenyl, 2-bromo-5-chlorophenyl, 3,4-dicyanophenyl, 3-trifluoromethyl-5-neopentylphenyl, 5-fluoro-2-methoxyphenyl, mesityl, 4-bromo-3,5-dimethylphenyl, 2-methyl-4-cyano-5-pentylphenyl, 2,5-dichloro-4-fluorophenyl, 2,4,6-triethoxyphenyl, and the like.

The phrase "(cycloalkyl)alkyl, containing . . . " includes, among others, cyclopropylmethyl, 6-(2-ethylcyclopropyl)hexyl, 2,3-dimethylcyclobutylmethyl, 7-cyclopentyl-2,2-dimethyloctyl, cyclohexylmethyl, 3-(3-isopropylcyclohexyl)propyl, 2-(1-methyl-4-ethylcyclooctyl)ethyl, 4-cycloundecylpentyl, and the like.

The phrases "phenylalkyl, containing . . . " and "diphenylalkyl, containing . . . " include, among others, benzyl, phenethyl, 4-(o-cumenyl)octyl, 3-(2-methyl-4-isohexyloxyphenyl)butyl, 1,3-dimethyl-6-(2-cyano-3-ethyl-5-fluorophenyl)heptyl, diphenylmethyl, 2-methyl-2-(m-tolyl)-3-(2,4-dichlorophenyl)propyl, and the like.

It will be understood that the present invention is not to be limited by the definitions and exemplification given herein. Various classes of compounds are contemplated, and such various classes of compounds can be employed in either the method or the insecticidal composition of the present invention. Examples of such contemplated various classes are given below. Each numbered subparagraph describes an independent class of compounds; in each class, the variables have the general meanings already given if not otherwise stated. Compounds wherein:

1. $R^1$ represents alkyl;
2. $R^1$ represents alkenyl;
3. $R^1$ represents alkadienyl;
4. $R^1$ represents cycloalkyl or substituted cycloalkyl;
5. $R^1$ represents cycloalkenyl or substituted cycloalkenyl;
6. $R^1$ represents cycloalkadienyl or substituted cycloalkadienyl;
7. $R^1$ represents phenyl or substituted phenyl;
8. $R^1$ represents (cycloalkyl)alkyl or (substituted cycloalkyl)alkyl;
9. $R^1$ represents phenylalkyl or (substituted phenyl)alkyl;
10. $R^1$ represents diphenylalkyl, phenyl(substituted phenyl)alkyl, or di(substituted phenyl)alkyl;
11. $R^1$ represents pyridyl, substituted pyridyl, piperidino, substituted piperidino, morpholino, pyrazinyl, or substituted pyrazinyl;
12. $R^1$ represents pyridylalkyl, (substituted pyridyl)alkyl, piperidinoalkyl, (substituted piperidino)alkyl, morpholinoalkyl, pyrazinylalkyl, (substituted pyrazinyl)alkyl, or tetrahydrofurylalkyl;
13. $R^1$ represents alkylamino, dialkylamino, phenylamino, diphenylamino, (phenyl)(alkyl)amino, (phenylalkyl)amino, di(phenylalkyl)amino, (phenyl)(phenylalkyl)amino, or (alkyl)(phenylalkyl)amino;
14. $R^1$ represents alkyl; phenyl, optionally substituted with $C_1$-$C_3$ alkyl, $C_1$-$C_3$ alkoxy, trifluoromethyl, or halo, or optionally disubstituted with halo; phenylalkyl, in which the phenyl moiety is unsubstituted; or 2-pyridylalkyl;
15. $R^1$ represents $C_1$-$C_6$ alkyl; phenyl, optionally monosubstituted with fluoro, chloro, or bromo, or optionally disubstituted with chloro; $C_7$-$C_{10}$ phenylalkyl, in which the phenyl moiety is unsubstituted; or 2-pyridylalkyl containing no more than about 7 carbon atoms, in which the pyridyl moiety is unsubstituted;
16. $R^1$ represents propyl;
17. $R^1$ represents phenyl;
18. $R^1$ represents o-tolyl, m-tolyl, p-tolyl, or 4-ethylphenyl;
19. $R^1$ represents 3-trifluoromethylphenyl;
20. $R^1$ represents 2-fluorophenyl, 3-fluorophenyl, 3-chlorophenyl, 4-chlorophenyl, 4-bromophenyl, 2,4-dichlorophenyl, or 3,4-dichlorophenyl;
21. $R^1$ represents benzyl, phenethyl, 3-phenylpropyl, or 2-chlorophenylmethyl;
22. $R^2$ represents hydrogen, $C_1$-$C_3$ alkyl, or phenyl;
23. $R^2$ represents hydrogen or $C_1$-$C_3$ alkyl;
24. $R^2$ represents hydrogen;
25. $R^3$ represents hydrogen, $C_1$-$C_3$ alkyl, or phenyl;
26. $R^3$ represents hydrogen or $C_1$-$C_3$ alkyl;
27. $R^3$ represents hydrogen;
28. $R^4$ represents hydrogen, $C_1$-$C_3$ alkyl, or phenyl;
29. $R^4$ represents hydrogen or $C_1$-$C_3$ alkyl;
30. $R^4$ represents hydrogen;
31. $R^5$ represents hydrogen, $C_1$-$C_3$ alkyl, or phenyl;
32. $R^5$ represents hydrogen or $C_1$-$C_3$ alkyl;
33. $R^5$ represents hydrogen;
34. $R^6$ represents halo, trifluoromethyl, or cyano;
35. $R^6$ represents chloro, bromo, trifluoromethyl, or cyano;
36. $R^6$ represents chloro or bromo;
37. $R^7$ represents hydrogen;
38. The variables are as described in subparagraphs 14 and 23;
39. The variables are as described in subparagraphs 14 and 24;
40. The variables are as described in subparagraphs 14 and 26;
41. The variables are as described in subparagraphs 14 and 27;
42. The variables are as described in subparagraphs 14 and 29;
43. The variables are as described in subparagraphs 14 and 30;
44. The variables are as described in subparagraphs 14 and 32;
45. The variables are as described in subparagraphs 14 and 33;
46. The variables are as described in subparagraphs 14 and 35;
47. The variables are as described in subparagraphs 14 and 36;
48. The variables are as described in subparagraphs 14 and 37;
49. The variables are as described in subparagraphs 15 and 24;
50. The variables are as described in subparagraphs 15 and 27;
51. The variables are as described in subparagraphs 15 and 30;
52. The variables are as described in subparagraphs 15 and 33;
53. The variables are as described in subparagraphs 15 and 36;
54. The variables are as described in subparagraphs 15 and 37;
55. The variables are as described in subparagraphs 14, 23, and 26;
56. The variables are as described in subparagraphs 14, 23, and 27;
57. The variables are as described in subparagraphs 14, 23, and 29;
58. The variables are as described in subparagraphs 14, 23, and 30;
59. The variables are as described in subparagraphs 14, 23, and 32;
60. The variables are as described in subparagraphs 14, 23, and 33;

61. The variables are as described in subparagraphs 14, 23, and 35;
62. The variables are as described in subparagraphs 14, 23, and 36;
63. The variables are as described in subparagraphs 14, 23, and 37;
64. The variables are as described in subparagraphs 14, 26, and 29;
65. The variables are as described in subparagraphs 14, 26, and 30;
66. The variables are as described in subparagraphs 14, 26, and 32;
67. The variables are as described in subparagraphs 14, 26, and 33;
68. The variables are as described in subparagraphs 14, 26, and 35;
69. The variables are as described in subparagraphs 14, 26, and 36;
70. The variables are as described in subparagraphs 14, 26, and 37;
71. The variables are as described in subparagraphs 14, 29, and 32;
72. The variables are as described in subparagraphs 14, 29, and 33;
73. The variables are as described in subparagraphs 14, 29, and 35;
74. The variables are as described in subparagraphs 14, 29, and 36;
75. The variables are as described in subparagraphs 14, 29, and 37;
76. The variables are as described in subparagraphs 14, 32, and 35;
77. The variables are as described in subparagraphs 14, 32, and 36;
78. The variables are as described in subparagraphs 14, 32, and 37;
79. The variables are as described in subparagraphs 15, 24, and 27;
80. The variables are as described in subparagraphs 15, 24, and 30;
81. The variables are as described in subparagraphs 15, 24, and 33;
82. The variables are as described in subparagraphs 15, 24, and 36;
83. The variables are as described in subparagraphs 15, 24, and 37;
84. The variables are as described in subparagraphs 15, 27, and 30;
85. The variables are as described in subparagraphs 15, 27, and 33;
86. The variables are as described in subparagraphs 15, 27, and 36;
87. The variables are as described in subparagraphs 15, 27, and 37;
88. The variables are as described in subparagraphs 15, 30, and 33;
89. The variables are as described in subparagraphs 15, 30, and 36;
90. The variables are as described in subparagraphs 15, 30, and 37;
91. The variables are as described in subparagraphs 15, 33, and 36;
92. The variables are as described in subparagraphs 15, 33, and 37;
93. The variables are as described in subparagraphs 15, 36, and 37;
94. The variables are as described in subparagraphs 14, 23, 26, and 29;
95. The variables are as described in subparagraphs 14, 23, 26, and 30;
96. The variables are as described in subparagraphs 14, 23, 26, and 32;
97. The variables are as described in subparagraphs 14, 23, 26, and 33;
98. The variables are as described in subparagraphs 14, 23, 26, and 35;
99. The variables are as described in subparagraphs 14, 23, 26, and 36;
100. The variables are as described in subparagraphs 14, 23, 26, and 37;
101. The variables are as described in subparagraphs 14, 23, 29, and 32;
102. The variables are as described in subparagraphs 14, 23, 29, and 33;
103. The variables are as described in subparagraphs 14, 23, 29, and 35;
104. The variables are as described in subparagraphs 14, 23, 29 and 36;
105. The variables are as described in subparagraphs 14, 23, 29, and 37;
106. The variables are as described in subparagraphs 14, 23, 32, and 35;
107. The variables are as described in subparagraphs 14, 23, 32, and 36;
108. The variables are as described in subparagraphs 14, 23, 32, and 37;
109. The variables are as described in subparagraphs 14, 23, 35, and 37;
110. The variables are as described in subparagraphs 14, 26, 29, and 32;
111. The variables are as described in subparagraphs 14, 26, 29, and 35;
112. The variables are as described in subparagraphs 14, 26, 29, and 37;
113. The variables are as described in subparagraphs 14, 26, 29, and 37;
114. The variables are as described in subparagraphs 14, 26, 32, and 35;
115. The variables are as described in subparagraphs 14, 26, 32, and 36;
116. The variables are as described in subparagraphs 14, 26, 32, and 37;
117. The variables are as described in subparagraphs 14, 26, 35, and 37;
118. The variables are as described in subparagraphs 14, 29, 32, and 35;
119. The variables are as described in subparagraphs 14, 29, 32, and 36;
120. The variables are as described in subparagraphs 14, 29, 32, and 37;
121. The variables are as described in subparagraphs 14, 29, 35, and 37;
122. The variables are as described in subparagraphs 15, 24, 27, and 30;
123. The variables are as described in subparagraphs 15, 24, 27, and 33;
124. The variables are as described in subparagraphs 15, 24, 27, and 36;
125. The variables are as described in subparagraphs 15, 24, 27, and 37;
126. The variables are as described in subparagraphs 15, 27, 30, and 33;
127. The variables are as described in subparagraphs 15, 27, 30, and 36;
128. The variables are as described in subparagraphs 15, 27, 30, and 37;

129. The variables are as described in subparagraphs 15, 30, 33, and 36;
130. The variables are as described in subparagraphs 15, 30, 33, and 37;
131. The variables are as described in subparagraphs 15, 33, 36, and 37;
132. The variables are as described in subparagraphs 14, 23, 26, 29, and 32;
133. The variables are as described in subparagraphs 14, 23, 26, 29, and 33;
134. The variables are as described in subparagraphs 14, 23, 26, 29, and 35;
135. The variables are as described in subparagraphs 14, 23, 26, 29, and 36;
136. The variables are as described in subparagraphs 14, 23, 26, 29, and 37;
137. The variables are as described in subparagraphs 14, 26, 29, 32, and 35;
138. The variables are as described in subparagraphs 14, 26, 29, 32, and 36;
139. The variables are as described in subparagraphs 14, 26, 29, 32, and 37;
140. The variables are as described in subparagraphs 14, 29, 32, 35, and 37;
141. The variables are as described in subparagraphs 15, 24, 27, 30, and 33;
142. The variables are as described in subparagraphs 15, 24, 27, 30, and 36;
143. The variables are as described in subparagraphs 15, 24, 27, 30, and 37;
144. The variables are as described in subparagraphs 15, 27, 30, 33, and 36;
145. The variables are as described in subparagraphs 15, 27, 30, 33, and 37;
146. The variables are as described in subparagraphs 15, 30, 33, 36, and 37;
147. The variables are as described in subparagraphs 14, 23, 26, 29, 32, and 35;
148. The variables are as described in subparagraphs 14, 23, 26, 29, 32, and 36;
149. The variables are as described in subparagraphs 14, 23, 26, 29, 32, and 37;
150. The variables are as described in subparagraphs 14, 23, 26, 29, 32, 35, and 37;
151. The variables are as described in subparagraphs 15, 24, 27, 30, 33, and 36;
152. The variables are as described in subparagraphs 15, 24, 27, 30, 33, and 37;
153. The variables are as described in subparagraphs 15, 24, 30, 33, 36, and 37;
154. The variables are as described in subparagraphs 15, 23, 26, 29, 32, 35, and 37; and
155. The variables are as described in subparagraphs 15, 24, 27, 30, 33, 36, and 37;

It should be apparent from the foregoing that any and all possible combinations of variables are within the scope of the present invention. From the above examples of contemplated classes, it is possible for one having ordinary skill in the art to construct any desired class, whether specifically exemplified or not. Thus, the present invention consists of multiple subgenera, with each subgenus consisting of a contemplated class of compounds as illustrated above without being limited thereto. Stated differently, any subgenus not specifically set forth herein is still implicitly within the scope of the present invention.

In order to further clarify the present invention, the following list of compounds is given by way of illustration. It is to be understood, however, that the present invention is neither confined to nor limited by the compounds listed.

1. 2-(2-ethylhexylamino)-N-(3-iodophenyl)-4,5-diphenyl-2-imidazoline-1-carbothioamide;
2. N-(3-bromophenyl)-2-(2-ethyl-1,4-dimethylheptylamino)-4-isopropyl-2-imidazoline-1-carbothioamide;
3. N-(3-chlorophenyl)-2-tetradecylamino-2-imidazoline-1-carbothioamide;
4. 2-(2-ethylhexadecylamino)-N-(3-fluorophenyl)-5-methyl-2-imidazoline-1-carbothioamide;
5. N-(3-bromophenyl)-2-vinylamino-2-imidazoline-1-carbothioamide;
6. 2-allylamino-N-[3-(1,1,2,2-tetrafluoroethoxy)-phenyl]-2-imidazoline-1-carbothioamide;
7. N-(3-cyanophenyl)-5-methyl-2-isopropenylamino-2-imidazoline-1-carbothioamide;
8. 2-(2-methyl-2-butenylamino)-4-methyl-5-phenyl-N-[3-(1,1,2,2-tetrafluoroethoxy)phenyl]-2-imidazoline-1-carbothioamide;
9. N-(3-chloro-5-fluorophenyl)-2-(1-octenylamino)-2-imidazoline-1-carbothioamide;
10. N-(3-bromophenyl)-4-isopropyl-2-(2,2,4,6,6-pentamethyl-3-heptenylamino)-2-imidazoline-1-carbothioamide;
11. N-(3-chlorophenyl)-2-(1,5-dimethyl-2-ethyl-3-propyl-4-nonenylamino)-2-imidazoline-1-carbothioamide;
12. N-(3-chlorophenyl)-2-(1-octadecenylamino)-2-imidazoline-1-carbothioamide;
13. 2-(1,3-butadienylamino)-4-ethyl-N-(3-iodophenyl)-2-imidazoline-1-carbothioamide;
14. N-(3-chlorophenyl)-2-(1,6-heptadienylamino)-2-imidazoline-1-carbothioamide;
15. 2-(7-methyl-2,4-octadienylamino)-5-phenyl-N-(3-trifluoromethylphenyl)-2-imidazoline-1-carbothioamide;
16. N-(3-fluorophenyl)-2-(6,8-tetradecadienylamino)-2-imidazoline-1-carbothioamide;
17. N-(3-cyano-4-ethylphenyl)-4-methyl-2-(2-methyl-7,10-heptadecadienylamino)-2-imidazoline-1-carbothioamide;
18. N-(3-chlorophenyl)-2-(2-methylcyclopropylamino)-2-imidazoline-1-carbothioamide;
19. 2-(2,3-diethylcyclopentylamino)-N-(3-fluorophenyl)-4-isopropyl-5-methyl-2-imidazoline-1-carbothioamide;
20. 2-cyclononylamino-N-[3-(1,1,2,2-tetrafluoroethoxy)-phenyl]-2-imidazoline-1-carbothioamide;
21. N-(3-cyanophenyl)-2-(5-propylcyclododecylamino)-4-phenyl-2-imidazoline-1-carbothioamide;
22. N-(3-chlorophenyl)-2-(2-ethyl-2-cyclopentenylamino)-2-imidazoline-1-carbothioamide;
23. N-(3-cyanophenyl)-2-(1-cyclohexenylamino)-4,5-diethyl-2-imidazoline-1-carbothioamide;
24. N-(3-chlorophenyl)-2-(3-chlorophenyl)-2-(3-isopropyl-5-methyl-2-cyclohexenylamino)-2-imidazoline-1-carbothioamide;
25. N-(3-chlorophenyl)-5-phenyl-2-(4-cyclononenylamino)-2-imidazoline-1-carbothioamide;
26. 2-(3-propyl-5-cyclododecenylamino)-N-[3-(1,1,2,2-tetrafluoroethoxy)phenyl]-2-imidazoline-1-carbothioamide;
27. N-(3-bromo-4-propylphenyl)-2-(1,3-cyclohexadienylamino)-2-imidazoline-1-carbothioamide;

28. N-(3,6-dichlorophenyl)-2-(3,5-dimethyl-2,4-cycloheptadienylamino)-4-methyl-2-imidazoline-1-carbothioamide;
29. 2-(3-ethyl-1,5-cyclodecadienylamino)-N-(3-trifluoromethylphenyl)-2-imidazoline-1-carbothioamide;
30. N-(3-chlorophenyl)-2-(1,7-cyclododecadienylamino)-2-imidazoline-1-carbothioamide;
31. N-(3-cyanophenyl)-2-(4-cyanophenylamino)-2-imidazoline-1-carbothioamide;
32. 2-(3-isohexylphenylamino)-N-(3-trifluoromethylphenyl)-2-imidazoline-1-carbothioamide;
33. 2-(3-t-butoxyphenylamino)-4,5-diethyl-N-(3-iodophenyl)-2-imidazoline-1-carbothioamide;
34. N-(3-chlorophenyl)-4-isopropyl-2-(4-pentylthiophenylamino)-2-imidazoline-1-carbothiomide;
35. N-(3-cyanophenyl)-4-ethyl-4-methyl-2-(2-methyl-4-isopropoxyphenylamino)-2-imidazoline-1-carbothioamide;
36. N-(3-bromophenyl)-2-(2-methylthio-4-trifluoromethylphenylamino)-2-imidazoline-1-carbothioamide;
37. 2-(3-cyano-5-ethyl-4-hexyloxyphenylamino)-N-(3-iodophenyl)-2-imidazoline-1-carbothioamide;
38. 2-(3-sec-butyl-2-fluoro-5-trifluoromethylphenylamino)-N-(3-chlorophenyl)-5-ethyl-2-imidazoline-1-carbothioamide;
39. 2-(2-cyclopropylhexylamino)-N-[3-(1,1,2,2-tetrafluoroethoxy)phenyl]-2-imidazoline-1-carbothioamide;
40. N-(3-bromophenyl)-2-[3-(3-ethylcycloheptyl)propylamino]-4-propyl-2-imidazoline-1-carbothioamide;
41. N-(3-chlorophenyl)-2-cyclododecylmethylamino-2-imidazoline-1-carbothioamide;
42. 2-[5-(4-ethyl-2-methyl-5-phenyl)hexylamino]-N-(3-fluorophenyl)-2-imidazoline-1-carbothioamide;
43. N-(3-chlorophenyl)-2-[3-(2-fluoro-4-hexyl-5-isopropylphenyl)propylamino]-4,5-dimethyl-2-imidazoline-1-carbothioamide;
44. N-(3-chlorophenyl)-2-diphenylmethylamino-2-imidazoline-1-carbothioamide;
45. 4,5-dimethyl-2-(2,4-diphenylbutylamino)-N-(3-iodophenyl)-2-imidazoline-1-carbothioamide;
46. 4-isopropyl-2-[1-phenyl-1-(3,5-dibromophenyl)ethylamino]-N-[3-(1,1,2,2-tetrafluoroethoxy)phenyl]-2-imidazoline-1-carbothioamide;
47. N-(3-chlorophenyl)-2-[2-(4-ethylthiophenyl)-3-(2-chloro-4-cyano-5-methylthiophenyl)propylamino]-2-imidazoline-1-carbothioamide;
48. N-(3-bromophenyl)-5-ethyl-2-(4-pyridylamino)-2-imidazoline-1-carbothioamide;
49. 2-(3-chloro-2-pyridylamino)-N-(3-trifluoromethylphenyl)-2-imidazoline-1-carbothioamide;
50. N-(3-chlorophenyl)-2-(5-ethyl-3-pyridylamino)-2-imidazoline-1-carbothioamide;
51. 2-(4-ethylpiperidinoamino)-N-(3-fluorophenyl)-5-methyl-2-imidazoline-1-carbothioamide;
52. N-(3,4-dichlorophenyl)-2-morpholinoamino-2-imidazoline-1-carbothioamide;
53. 2-pyrazinylamino-N-(3-trifluoromethylphenyl)-2-imidazoline-1-carbothioamide;
54. N-(4-fluoro-3-iodophenyl)-2-(5-isopropyl-2-pyrazinylamino)-4-methyl-2-imidazoline-1-carbothioamide;
55. N-(3-chlorophenyl)-2-[5-(6-methoxy-3-pyridylheptylamino]-2-imidazoline-1-carbothioamide;
56. N-(3-fluorophenyl)-2-[2-(3-methyl-5-neohexylpiperidino)propylamino]-2-imidazoline-1-carbothioamide;
57. N-(3-chlorophenyl)-2-(12-piperidinododecylamino)-2-imidazoline-1-carbothioamide;
58. N-(3-chlorophenyl)-2-morpholinomethyl-4-methyl-2-imidazoline-1-carbothioamide;
59. 2-(2-ethyl-5-morpholinohexylamino)-N-(3-fluorophenyl)-2-imidazoline-1-carbothioamide;
60. N-(3-cyanophenyl)-2-[1-methyl-2-(2-pyrazinyl)ethylamino]-2-imidazoline-1-carbothioamide;
61. N-(3-chlorophenyl)-4-methyl-2-[9-(4-methyl-2-pyrazinyl)nonylamino]-2-imidazoline-1-carbothioamide;
62. 2-[2-ethyl-4-(3-tetrahydrofuryl)hexylamino]-N-(3-fluorophenyl)-2-imidazoline-1-carbothioamide;
63. N-(3-iodophenyl)-5-propyl-2-[13-(2-tetrahydrofuryl)tridecylamino]-2-imidazoline-1-carbothioamide;
64. 2-dodecylamino-5-isopropyl-N-(3-trifluoromethylphenyl)-2-imidazoline-1-carbothioamide;
65. N-(3-bromophenyl)-2-dimethylamino-5-ethyl-5-methyl-4-propyl-2-imidazoline-1-carbothioamide;
66. N-(3-cyanophenyl)-2-(3-methoxyphenylamino)-5-methyl-2-imidazoline-1-carbothioamide;
67. N-(3-chlorophenyl)-2-(N-phenyl-N-2,3-dibromophenylamino)-2-imidazoline-1-carbothioamide;
68. 4-methyl-2-(N-phenyl-N-hexylamino)-N-[3-(1,1,2,2-tetrafluoroethoxy)phenyl]-2-imidazoline-1-carbothioamide;
69. N-(3-cyanophenyl)-2-(N²-phenylhydrazino)-2-imidazoline-1-carbothioamide;
70. N-(3-fluorophenyl)-2-{N²-[2-methyl-2-(4-ethylphenyl)propyl]-N²-(7-phenyldodecyl)hydrazino}-2-imidazoline-1-carbothioamide;
71. 2-[N²-benzyl-N²-(3-isopropylthiophenyl)hydrazino]-N-(3-fluorophenyl)-5-phenyl-2-imidazoline-1-carbothioamide;
72. N-(3-chlorophenyl)-2-[N²-(2-ethyloctyl)-N²-(2-phenylpentyl)hydrazino]-2-imidazoline-1-carbothioamide;

The compounds of the present invention are prepared in accordance with methods well known to those having ordinary skill in the art. In general, the compounds can be prepared by reacting an appropriately-substituted 2-amino-2-imidazoline with an equivalent amount of a suitably-substituted phenyl isothiocyanate, as shown by the following equation:

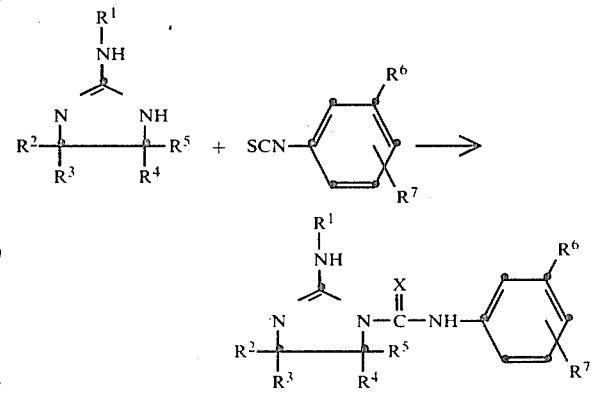

wherein the variables are as defined hereinbefore. The reaction typically is carried out at ambient temperature for approximately 14 hours in a suitable solvent. If desired, shorter reaction times will result by heating the reaction mixture at an elevated temperature, up to and including the reflux temperature of the reaction mixture. Suitable solvents include, among others, benzene, toluene, the xylenes, chloroform, ethyl acetate, acetonitrile, and the like. Chloroform is the solvent of choice. The reaction mixture then is worked up in accordance with the usual procedures. Typically, the solvent is removed under reduced pressure and the residue recrystallized from a suitable solvent or solvent combination. The most frequently used recrystallization solvents and solvent combinations are benzene, hexane, benzene/hexane, chloroform/hexane, ethyl acetate/hexane, and aqueous ethanol.

The phenyl isothiocyanate starting materials are readily prepared by known methods from the corresponding amines (anilines). For example, the appropriately-substituted amine is reacted with N,N-dimethylthiocarbamoyl chloride in a suitable solvent, such as benzene, toluene, or a xylene. Typically, the reaction is carried out at reflux temperature for approximately 14 hours. The resulting phenyl isothiocyanate normally is isolated and purified by distillation. Alternatively, the appropriately-substituted aniline can be reacted with thiophosgene in chloroform in the presence of aqueous sodium carbonate at a temperature of 10°-15° C.

The 2-amino-2-imidazoline starting materials also are prepared in accordance with known procedures. When $R^1$ is phenyl or substituted phenyl, the 2-amino-2-imidazolines are prepared generally in accordance with the following equation:

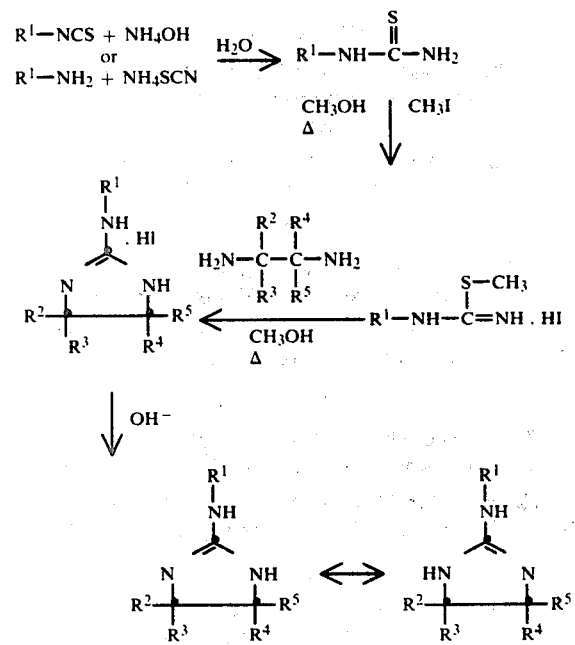

wherein the variables are as defined hereinbefore; see, e.g., German Published Application OLS No. 1,303,930. First, a phenyl isothiocyanate is treated with ammonium hydroxide to give the corresponding thiourea. Alternatively, the thiourea is obtained by reacting an aniline with ammonium thiocyanate. The thiourea then is alkylated with methyl iodide under reflux conditions in methanol. The resulting thiouronium salt, which normally is not isolated, is reacted with an appropriately-substituted ethylenediamine to give the desired 2-amino-2-imidazoline as the hydriodide salt; the salt can be treated with base to give the free imidazoline. The reaction of the thiouronium salt with the ethylenediamine typically is carried out in methanol at a temperature up to and including the reflux temperature of the reaction mixture. Reaction times typically run from about 48 to about 72 hours. It often is necessary to chromatograph the free imidazoline over alumina, using ethyl acetate as eluant.

An alternate procedure for the preparation of the 2-amino-2-imidazolines consists of reacting a phenyl isothiocyanate with chlorine to give the corresponding isocyanide dichloride. This reaction typically is carried out at the reflux temperature of the reaction mixture, using a suitable solvent, such as methylene dichloride or 1,2-dichloroethane. The isocyanide dichloride then is treated with an ethylenediamine as described hereinabove. The preparation of the isocyanide dichloride is described in U.S. Pat. No. 3,468,887.

A third method for preparing the 2-amino-2-imidazolines consists of treating the phenyl isothiocyanate directly with the ethylenediamine at the reflux temperature of the reaction medium, using a solvent such as chlorobenzene. This reaction gives the desired product directly, but is not a clean reaction and therefore is not preferred.

When $R^1$ is other than phenyl or substituted phenyl, the desired 2-amino-2-imidazolines are readily obtained, again in accordance with known procedures, by the reaction scheme shown below:

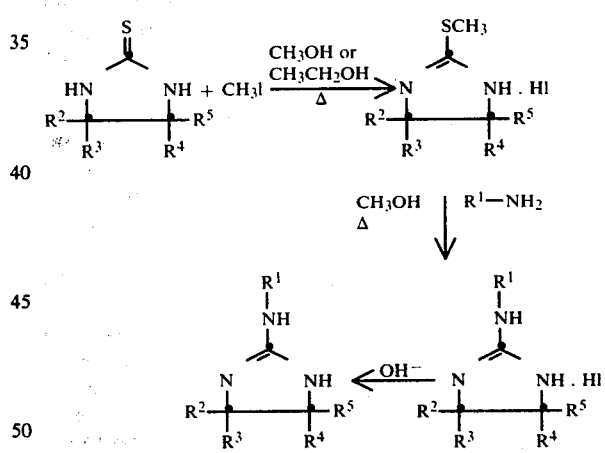

wherein the variables are as defined hereinbefore; see, e.g., S. R. Aspinall et al., J. Amer. Chem. Soc., 73, 602 (1951). The appropriately-substituted 2-imidazolidinethione is S-alkylated, typically with methyl iodide in methanol or ethanol, at an elevated temperature which usually is the reflux temperature of the reaction mixture. The resulting compound, as the hydriodide salt, then is reacted with the desired amine, again usually in methanol, at the reflux temperature of the reaction medium for a period of from about 48 to about 72 hours, to give the desired 2-amino-2-imidazolien, again as the hydriodide salt. When $R^2$, $R^3$, $R^4$, and $R^5$ all are hydrogen, the 2-imidazolidinethione is a commercially-available material. However, the substituted 2-imidazolidinethiones are readily obtained by methods well known to those having ordinary skill in the art.

Those having ordinary skill in the art will recognize that the 2-amino-2-imidazolines can exist in either of two tautomeric forms. When the imidazoline is symmetrical, i.e., the substituents at the 4-position are the same as those in the 5-position, the two tautomeric forms are equivalent and only one product will result upon reacting the symmetrical imidazoline with a phenyl isothiocyanate. Unsymmetrical imidazolines, however, can give two isomeric products, although one isomer usually is favored and predominates. Thus, for example, the reaction of 2-hexylamino-4-methyl-4-imidazoline with m-chlorophenyl isothiocyanate can give N-(3-chlorophenyl)-2-hexylamino-4-methyl-2-imidazoline-1-carbothioamide and N-(3-chlorophenyl)-2-hexylamino-5-methyl-2-imidazoline-1-carbothioamide. When unsymmetrical imidazolines are employed, the resulting isomeric products usually can be separated by means of liquid chromatography, typically on silica gel with toluene or ethyl acetate as eluant.

The examples which follow illustrate the preparations of representative compounds of the present invention. In each case, the compound was identified by elemental microanalysis and nuclear magnetic resonance analysis. Unless stated otherwise, all temperatures are given in degrees Celsius.

EXAMPLE 1

Preparation of N-(3-chlorophenyl)-2-methylamino-2-imidazoline-1-carbothioamide

A mixture of 2.0 g. of 2-methylamino-2-imidazoline and 3.4 g. of m-chlorophenyl isothiocyanate in approximately 75 ml. of chloroform was stirred for about 62 hours at ambient temperature. Hexane was added to the reaction mixture and the solid which precipitated was isolated by filtration. The solid was recrystallized from aqueous ethanol to give 2 g. (37%) of N-(3-chlorophenyl)-2-methylamino-2-imidazoline-1-carbothioamide, m.p. 156°–8°. The following elemental microanalysis was obtained:

Calculated for $C_{11}H_{13}ClN_4S$: C, 49.16; H, 4.88; N, 20.85. Found: C, 49.02; H, 4.93; N, 20.73.

Each of the following compounds was prepared in accordance with the general procedure of Example 1, using the appropriately-substituted 2-amino-2-imidazoline and phenyl isothiocyanate. In each case, the reaction was carried out in chloroform for a period from about 14 to about 62 hours at ambient temperature. When available, the percent yield, melting point, recrystallization solvent, and elemental microanalysis are given for each compound.

EXAMPLE 2.

N-(3-chlorophenyl)-2-propylamino-2-imidazoline-1-carbothioamide, 132°–4°, aqueous ethanol Calculated for $C_{13}H_{17}ClN_4S$: C, 52.61; H, 5.77; N, 18.88. Found: C, 52.37; H, 5.71; N, 18.80.

EXAMPLE 3.

N-(3-chlorophenyl)-2-hexylamino-2-imidazoline-1-carbothioamide, 75%, 96°–8°, ethanol Calculated for $C_{16}H_{23}ClN_4S$: C, 56.71; H, 6.84; N, 16.53. Found: C, 56.68; H, 6.73; N, 16.64.

EXAMPLE 4.

N-(3-chlorophenyl)-2-cyclohexylamino-2-imidazoline-1-carbothioamide, 62%, 178°–80°, ethanol Calculated for $C_{16}H_{21}ClN_4S$: C, 57.04; H, 6.28; N, 16.63. Found: C, 56.98; H, 5.98; N, 16.39.

EXAMPLE 5.

N-(3-fluorophenyl)-2-phenylamino-2-imidazoline-1-carbothioamide, 99%, 175°–7°, ethanol Calculated for $C_{16}H_{15}FN_4S$: C, 61.13; H, 4.81; N, 17.82. Found: C, 60.98; H, 4.91; N, 17.70.

EXAMPLE 6.

N-(3-chlorophenyl)-2-phenylamino-2-imidazoline-1-carbothioamide, 123°–4°, benzene Calculated for $C_{16}H_{15}ClN_4S$: C, 58.09; H, 4.57; N, 16.93. Found: C, 57.89; H, 4.73; N, 16.79.

EXAMPLE 7.

N-(3-bromophenyl)-2-phenylamino-2-imidazoline-1-carbothioamide, 80%, 166°–7°, ethanol Calculated for $C_{16}H_{15}BrN_4S$: C, 51.21; H, 4.03; N, 14.93. Found: C, 51.43; H, 4.05; N, 14.92.

EXAMPLE 8.

N-(3-iodophenyl)-2-phenylamino-2-imidazoline-1-carbothioamide, 97%, 126°–8°, ethanol Calculated for $C_{16}H_{15}IN_4S$: C, 45.51; H, 3.58; N, 13.27. Found: C, 45.27; H, 3.55; N, 13.15.

EXAMPLE 9.

2-Phenylamino-N-(3-trifluoromethylphenyl)-2-imidazoline-1-carbothioamide, 130°–1°, aqueous ethanol Calculated for $C_{17}H_{15}F_3N_4S$: C, 56.04; H, 4.15; N, 15.38. Found: C, 55.82; H, 4.21; N, 15.36.

EXAMPLE 10.

N-(3-Cyanophenyl)-2-phenylamino-2-imidazoline-1-carbothioamide, 90%, 175°–6°, ethanol Calculated for $C_{17}H_{15}N_5S$: C, 63.53; H, 4.70; N, 21.79. Found: C, 63.47; H, 4.66; N, 21.65.

EXAMPLE 11.

N-(3-Chlorophenyl)-2-(2-methylphenylamino)-2-imidazoline-1-carbothioamide, 68%, 107°–9°, ethanol Calculated for $C_{17}H_{17}ClN_4S$: C, 59.21; H, 4.97; N, 16.25. Found: C, 59.30; H, 5.08; N, 16.28.

EXAMPLE 12.

N-(3-Chlorophenyl)-2-(3-methylphenylamino)-2-imidazoline-1-carbothioamide, 76%, 101°–3°, ethanol Calculated for $C_{17}H_{17}ClN_4S$: C, 59.21; H, 4.97; N, 16.25. Found: C, 59.35; H, 4.79; N, 16.17.

EXAMPLE 13.

2-(3-Methylphenylamino)-N-(3-trifluoromethylphenyl)-2-imidazoline-1-carbothioamide, 90%, 113°–5°, aqueous ethanol Calculated for $C_{18}H_{17}F_3N_4S$: C, 57.13; H, 4.53; N, 14.81. Found: C, 56.81; H, 4.40; N, 14.71.

EXAMPLE 14.

N-(3-Chlorophenyl)-2-(4-methylphenylamino)-2-imidazoline-1-carbothioamide, 76%, 98°–100°, ethanol Calculated for $C_{17}H_{17}ClN_4S$: C, 59.21; H, 4.97; N, 16.25. Found: C, 59.43; H, 4.76; N, 16.09.

EXAMPLE 15.

N-(3-Chlorophenyl)-2-(2-ethylphenylamino)-2-imidazoline-1-carbothioamide, 112°–3°, ethanol Calculated for $C_{18}H_{19}ClN_4S$: C, 61.24; H, 5.34; N, 15.61. Found: C, 60.02; H, 5.28; N, 15.34.

EXAMPLE 16.

N-(3-Chlorophenyl)-2-(4-ethylphenylamino)-2-imidazoline-1-carbothioamide, 63%, 114°–5°, aqueous ethanol Calculated for $C_{18}H_{19}ClN_4S$: C, 60.24; H, 5.34; N, 15.61. Found: C, 60.41; H, 5.21; N, 15.46.

EXAMPLE 17.

N-(3-Chlorophenyl)-2-(2-methoxyphenylamino)-2-imidazoline-1-carbothioamide, 154°–6°, ethanol Calculated for $C_{17}H_{17}ClON_4S$: C, 56.58; H, 4.75; N, 15.53. Found: C, 56.29; H, 4.59; N, 15.48.

EXAMPLE 18.

N-(3-Chlorophenyl)-2-(4-methoxyphenylamino)-2-imidazoline-1-carbothioamide, 86%, 149°–50°, ethanol Calculated for $C_{17}H_{17}ClON_4S$: C, 56.58; H, 4.75; N, 15.53. Found: C, 56.59; H, 4.55; N, 15.62.

EXAMPLE 19.

N-(3-Chlorophenyl)-2-(3-methylthiophenylamino)-2-imidazoline-1-carbothioamide, 147°–8°, ethanol Calculated for $C_{17}H_{17}ClN_4S_2$: C, 54.17; H, 4.55; N, 14.86. Found: C, 53.98; H, 4.47; N, 14.70.

EXAMPLE 20.

N-(3-Chlorophenyl)-2-(2-fluorophenylamino)-2-imidazoline-1-carbothioamide, ethanol Calculated for $C_{16}H_{14}ClN_4S$: C, 55.09; H, 4.05; N, 16.06. Found: C, 55.19; H, 4.06; N, 16.29.

EXAMPLE 21.

N-(3-Chlorophenyl)-2-(3-fluorophenylamino)-2-imidazoline-1-carbothioamide, 77%, 151°–3°, ethanol Calculated for $C_{16}H_{14}ClFN_4S$: C, 55.09; H, 4.05; N, 16.06. Found: C, 55.18; H, 3.86; N, 16.33.

EXAMPLE 22.

N-(3-Bromophenyl)-2-(3-fluorophenylamino)-2-imidazoline-1-carbothioamide, 71%, 146°–8°, ethanol Calculated for $C_{16}H_{14}BrFN_4S$: C, 48.86; H, 3.59; N, 14.25. Found: C, 48.71; H, 3.56; N, 14.23.

EXAMPLE 23.

N-(3,4-Dichlorophenyl)-2-(3-fluorophenylamino)-2-imidazoline-1-carbothioamide, 84%, product not recrystallized Calculated for $C_{16}H_{13}Cl_2FN_4S$: C, 50.14; H, 3.42; N, 14.62 Found: C, 49.96; H, 3.66; N, 14.41

EXAMPLE 24.

N-(3-Chlorophenyl)-2-(4-fluorophenylamino)-2-imidazoline-1-carbothioamide, 170°–1°, ethanol Calculated for $C_{16}H_{14}ClFN_4S$: C, 55.09; H, 4.05; N, 16.06. Found: C, 54.95; H, 4.07; N, 15.90.

EXAMPLE 25.

N-(3-Chlorophenyl)-2-(2-chlorophenylamino)-2-imidazoline-1-carbothioamide, 90%, 145°–6°, ethanol Calculated for $C_{16}H_{14}Cl_2N_4S$: C, 52.61; H, 3.86; N, 15.34. Found: C, 52.66; H, 3.80; N, 15.10.

EXAMPLE 26.

N-(3-Bromophenyl)-2-(2-chlorophenylamino)-2-imidazoline-1-carbothioamide, 89%, 158°–60°, ethanol Calculated for $C_{16}H_{14}BrClN_4S$: C, 46.90; H, 3.44; N, 13.67. Found: C, 46.69; H, 3.29; N, 13.40.

EXAMPLE 27.

N-(3-Chlorophenyl)-2-(3-chlorophenylaminp)-2-imidazoline-1-carbothioamide, chromatographed on silica gel with benzene as eluant Calculated for $C_{16}H_{14}Cl_2N_4S$: C, 52.61; H, 3.86; N, 15.34. Found: C, 52.51; H, 3.99; N, 15.42.

EXAMPLE 28.

N-(3-Bromophenyl)-2-(3-chlorophenylamino)-2-imidazoline-1-carbothioamide, 137°–9°, ethanol Calculated for $C_{16}H_{14}BrClN_4S$: C, 46.90; H, 3.44; N, 13.67. Found: C, 47.12; H, 3.46; N, 13.54.

EXAMPLE 29.

N-(3-Chlorophenyl)-2-(4-chlorophenylamino)-2-imidazoline-1-carbothioamide, 82%, 141°–3°, ethanol Calculated for $C_{16}H_{14}Cl_2N_4S$: C, 52.61; H, 3.86; N, 15.34. Found: C, 52.42; H, 3.83; N, 15.21.

EXAMPLE 30.

N-(3-chloro-4-methylphenyl)-2-(4-chlorophenylamino)-2-imidazoline-1-carbothioamide, 135°–7°, ethanol Calculated for $C_{17}H_{16}Cl_2N_4S$: C, 53.83; H, 4.25; N, 14.77. Found: C, 53.54; H, 3.97; N, 14.55.

EXAMPLE 31.

2-(2-Bromophenylamino)-N-(3-chlorophenyl)-2-imidazoline-1-carbothioamide, 179°–81°, ethanol

EXAMPLE 32.

2-(3-Bromophenylamino)-N-(3-chlorophenyl)-2-imidazoline-1-carbothioamide, 157°–9°, ethanol Calculated for $C_{16}H_{14}BrClN_4S$: C, 46.90; H, 3.44; N, 13.67. Found: C, 47.00; H, 3.63; N, 13.57.

EXAMPLE 33.

N-(3-Bromophenyl)-2-(3-bromophenylamino)-2-imidazoline-1-carbothioamide, 73%, 161°–3° C., ethanol Calculated for $C_{16}H_{14}Br_2N_4S$: C, 42.31; H, 3.11; N, 12.34. Found: C, 42.36; H, 3.11; N, 12.37.

EXAMPLE 34.

2-(4-Bromophenylamino)-N-(3-chlorophenyl)-2-imidazoline-1-carbothioamide, 136°-8°, ethanol Calculated for $C_{16}H_{14}BrClN_4S$: C, 46.90; H, 3.44; N, 13.67. Found: C, 46.69; H, 3.33; N, 13.47.

EXAMPLE 35.

N-(3-Chlorophenyl)-2-(3-trifluoromethylphenylamino)-2-imidazoline-1-carbothioamide, 14%, 175°-7°, ethanol Calculated for $C_{17}H_{14}ClF_3N_4S$: C, 51.20; H, 3.54; N, 14.05. Found: C, 51.38; H, 3.68; N, 14.11.

EXAMPLE 36.

N-(3-Chlorophenyl)-2-(5-fluoro-2-methylphenylamino)-2-imidazoline-1-carbothioamide, 64%, 142°-4°, ethanol Calculated for $C_{17}H_{16}ClFN_4S$: C, 56.27; H, 4.44; N, 15.44. Found: C, 56.07; H, 4.25; N, 15.24.

EXAMPLE 37.

2-(3-Chloro-2-methylphenylamino)-N-(3-chlorophenyl)-2-imidazoline-1-carbothioamide, 77%, 165°-7°, ethanol Calculated for $C_{17}H_{16}Cl_2N_4S$: C, 53.83; H, 4.25; N, 14.77. Found: C, 53.55; H, 4.09; N, 14.57.

EXAMPLE 38.

2-(5-Chloro-2-methylphenylamino)-N-(3-chlorophenyl)-2-imidazoline-1-carbothioamide, 149°-51°, ethanol Calculated for $C_{17}H_{16}Cl_2N_4S$: C, 53.83; H, 4.25; N, 14.77. Found: C, 53.36; H, 4.13; N, 14.92.

EXAMPLE 39.

2-(2-Chloro-3-methylphenylamino)-N-(3-fluorophenyl)-2-imidazoline-1-carbothioamide, 32%, 153°-5°, benzene Calculated for $C_{17}H_{16}ClFN_4S$: C, 56.27; H, 4.44; N, 15.44. Found: C, 56.19; H, 4.41; N, 15.25.

EXAMPLE 40.

2-(2-Chloro-3-methylphenylamino)-N-(3-chlorophenyl)-2-imidazoline-1-carbothioamide, 75%, 160°-2°, ethanol Calculated for $C_{17}H_{16}Cl_2N_4S$: C, 53.83; H, 4.25; N, 14.77. Found: C, 53.62; H, 3.99; N, 14.57.

EXAMPLE 41.

N-(3-Chlorophenyl)-2-(2,4-dichlorophenylamino)-2-imidazoline-1-carbothioamide, 134°-5°, aqueous ethanol Calculated for $C_{16}H_{13}Cl_3N_4S$: C, 48.08; H, 3.28; N, 14.02. Found: C, 48.27; H, 3.04; N, 14.29.

EXAMPLE 42.

N-(3-Chlorophenyl)-2-(3,4-dichlorophenylamino)-2-imidazoline-1-carbothioamide, 79%, 159°-60°, ethanol Calculated for $C_{16}H_{13}Cl_3N_4S$: C, 48.08; H, 3.28; N, 14.02. Found: C, 47.87; H, 3.24; N, 13.99.

EXAMPLE 43.

N-(3-Bromophenyl)-2-(3,4-dichlorophenylamino)-2-imidazoline-1-carbothioamide, 55%, 165°-6°, ethanol Calculated for $C_{16}H_{13}BrCl_2N_4S$: C, 43.27; H, 2.95; N, 12.61. Found: C, 43.36; H, 2.98; N, 12.54.

EXAMPLE 44.

N-(3-Chlorophenyl)-2-(3,5-dichlorophenylamino)-2-imidazoline-1-carbothioamide, 150°-2°, ethanol Calculated for $C_{16}H_{13}Cl_3N_4S$: C, 48.08; H, 3.28; N, 14.02. Found: C, 48.03; H, 3.52; N, 13.91.

EXAMPLE 45.

2-Benzylamino-N-(3-fluorophenyl)-2-imidazoline-1-carbothioamide, 131°-3°, ethanol Calculated for $C_{17}H_{17}FN_4S$: C, 62.17; H, 5.22; N, 17.06. Found: C, 61.91; H, 4.99; N, 16.85.

EXAMPLE 46.

2-Benzylamino-N-(3-chlorophenyl)-2-imidazoline-1-carbothioamide, 11%, 133°-5°, benzene/hexane Calculated for $C_{17}H_{17}ClN_4S$: C, 59.21; H, 4.97; N, 16.25. Found: C, 59.09; H, 4.79; N, 16.46.

EXAMPLE 47.

2-Benzylamino-N-(3-trifluoromethylphenyl)-2-imidazoline-1-carbothioamide, 109°-11°, chloroform/hexane Calculated for $C_{18}H_{17}F_3N_4S$: C, 57.13; H, 4.53; N, 14.81. Found: C, 57.42; H, 4.65; N, 15.05.

EXAMPLE 48.

N-(3-Chlorophenyl)-2-(2-chlorophenylmethylamino)-2-imidazoline-1-carbothioamide, 54%, 148°-50°, ethanol Calculated for $C_{17}H_{16}Cl_2N_4S$: C, 53.83; H, 4.25; N, 14.77. Found: C, 53.68; H, 4.26; N, 14.84.

EXAMPLE 49.

N-(3-Chlorophenyl)-2-phenethylamino-2-imidazoline-1-carbothioamide, 127°-9°, aqueous ethanol Calculated for $C_{18}H_{19}ClN_4S$: C, 60.24; H, 5.34; N, 15.61. Found: C, 60.21; H, 5.34; N, 15.54.

EXAMPLE 50.

N-(3-Chlorophenyl)-2-(3-phenylpropylamino)-2-imidazoline-1-carbothioamide, 47%, 89°-81°, ethanol Calculated for $C_{19}H_{21}ClN_4S$: C, 61.20; H, 5.68; N, 15.02. Found: C, 60.98; H, 5.44; N, 15.27.

EXAMPLE 51.

N-(3-Chlorophenyl)-2-(4-phenylbutylamino)-2-imidazoline-1-carbothioamide, 87°-9°, ethanol Calculated for $C_{20}H_{23}ClN_4S$: C, 62.08; H, 5.99; N, 14.48. Found: C, 62.08; H, 6.03; N, 14.41.

EXAMPLE 52.

N-(3-Chlorophenyl)-2-(2-pyridylmethylamino)-2-imidazoline-1-carbothioamide, 23%, 157°-60°, ethanol Calculated for $C_{16}H_{16}ClN_5S$: C, 55.57; H, 4.66; N, 20.25. Found: C, 55.84; H, 4.83; N, 19.95.

EXAMPLE 53.

N-(3-Chlorophenyl)-2-[2-(2-pyridyl)ethylamino]-2-imidazoline-1-carbothioamide, 115°–7°, ethanol Calculated for $C_{17}H_{18}ClN_5S$: C, 56.74; H, 5.04; N, 19.46. Found: C, 56.80; H, 4.83; N, 19.65.

As already indicated, the compounds of the present invention are useful for the control of insects. For example, the compounds are active against such insects as Mexican bean beetle, boll weevil, corn rootworm, cereal leaf beetle, flea beetle, borers, Colorado potatoe beetle, grain beetles, alfalfa weevil, carpet beetle, confused flour beetle, powder post beetle, wireworms, rice weevil, rose beetle, plum curculio, white grubs, melon aphid, rose aphid, white fly, grain aphid, corn leaf aphid, pea aphid, mealybugs, scales, leafhopper, citrus aphid, spotted alfalfa aphid, green peach aphid, bean aphid, milkweed bug, tarnished plant bug, box elder bug, bedbug, squash bug, chinch bug, house fly, yellow fever mosquito, stable fly, horn fly, cabbage maggot, carrot rust fly, codling moth, cutworm, clothes moth, Indian meal moth, leafrollers, corn earworm, European corn borer, cabbage looper, cotton bollworm, bagworm, sod webworm, fall armyworm, German cockroach, and American cockroach.

Because the compounds of the present invention appear to function most effectively when ingested by the target insect, such compounds are particularly useful for the control of insect pests on plants, and especially for the control of Mexican bean beetles. In general, however, the compounds of the present invention can be applied to or incorporated into any food or water source for the target insect.

Thus, the present invention provides a method for reducing or eradicating a population of the insect species *Epilachna varivestis* which comprises administering to the insect by ingestion an insecticidally-effective amount of a compound of the present invention.

The term "insecticidally-effective amount" refers to an amount which results in the inactivation of the insect. Such inactivation can be lethal, either immediately or with delay, or it can be a sub-lethal inactivation in which the insect is rendered incapable of carrying out one or more of its normal life processes. Thus, the term "reducing or eradicating" means that the compound of the present invention can either kill all of the insect species to which the compound is applied, or that the application of the compound reduces the population of such insect species. As is well known in the art, many known insecticides render the insect incapable of carrying out one or more of its normal life processes. Most often, the nervous system typically is seriously disturbed. However, the precise mechanism by which the compounds constituting the present invention function is not yet known, and the insecticidal method of the present invention is not limited by any mode of operation.

The utilization of an inactivating amount of one of the compounds of the present invention is critical to the insecticidal methods of the present invention. The inactivating amount sometimes can be administered by employing the compound in unmodified form. However, for best results, it generally is necessary that the compound or compounds be employed in modified form; that is, as one component of a composition formulated to implement the insecticidal effects. Thus, for example, the active ingredient can be mixed with water or other liquid or liquids, preferably aided by the usage of a surface-active agent. The compounds also can be incorporated on a finely-divided solid, which can be a substance having surface-active adsorption properties, to yield a wettable powder which subsequently can be dispersed in water or other liquid or incorporated as part of a dust which can be applied directly. Other methods of formulation are known in the art and can be employed in implementing the present invention.

The exact concentration of one or more of the compounds of the present invention in a composition thereof with one or a plurality of adjuvants can vary; it is necessary only that one or more of the products be present in such amount as to make possible the application of an inactivating dosage to an insect. In many situations, a composition comprising 0.001% of the present active agent is effective for the administration of an inactivating amount thereof to insect pests. Compositions having a higher concentration of active agent, such as a concentration of from about 0.001 to about 0.5% can, of course, be employed. In still other operations, compositions containing from about 0.5 to about 98% by weight of one compound or from about 0.5 to about 98% of a total of more than one compound, are conveniently employed. Such compositions are adapted to be employed as treating compositions per se or as concentrates for subsequent dilution with additional adjuvant to produce ultimate treating compositions.

Liquid compositions containing the desired amount of active agent are prepared by dissolving the substance in an organic liquid or by dispersing the substance in water with or without the aid of a suitable surface-active dispersing agent such as an ionic or nonionic emulsifying agent. Such compositions also can contain modifying substances which serve to aid spreading and adhesion of the material on plant foliage. Suitable organic liquid carriers include the agricultural spray oils and the petroleum distillates such as diesel fuel, kerosene, fuel oil, naphthas, and Stoddard solvent. Among such liquids the petroleum distillates are generally preferred. The aqueous compositions can contain one or more water-immiscible solvents for the toxicant compounds. In such aqueous compositions, the carrier comprises an aqueous emulsion, e.g., a mixture of water, emulsifying agents, and water-immiscible solvents. The choice of dispersing and emulsifying agent and the amount thereof employed is dictated by the nature of the composition and by the ability of the agent to facilitate the dispersing of the active agent in the carrier to produce the desired composition. Dispersing and emulsifying agents which can be employed in the compositions include the condensation products of alkylene oxides with phenols and organic acids, alkaryl sulfonates, polyoxyalkylene derivatives of sorbitan esters, complex ether alcohols, and the like. For a review of known surface active agents which are suitably employed in implementing the present invention, attention is directed to U.S. Pat. No. 3,095,299, second column, lines 25–36, and references cited therein.

In the preparation of dust compositions, the active ingredient is intimately dispersed in and on a finely-divided solid such as clay, talc, chalk, gypsum, limestone, vermiculite fines, perlite, and the like. In one method of achieving such dispersion, the finely-divided carrier is mechanically mixed or ground with the active agent.

Similarly, dust compositions containing the toxicant compound can be prepared with various solid carriers such as bentonite, fuller's earth, attapulgite, and other clays having surface-active adsorptive properties. Depending upon the proportions of ingredients, these dust compositions can be employed as concentrates and subsequently diluted with additional adsortive-type solid carriers or with chalk, talc, or gypsum, or the like to obtain the desired amount of active ingredient in a composition adapted to be employed in accordance with the present invention. Also, such dust compositions can be dispersed in water, with or without the aid of a dispersing agent, to form spray mixtures.

Also, the compositions of the present invention can be employed in granular formulations. These formulations are prepared in conventional manner, typically by dissolving the compound in a solvent with or without a surface-active agent and spraying or otherwise distributing the resulting solution onto pre-formed granules. Such granular formulations are capable of providing longer-lasting activity and may be preferred for crops such as corn where repeated application is not practical.

When operating in accordance with the present invention, one or more of the compounds or a composition containing one or more of the compounds is applied to a source of food or water of the pest to be controlled in any convenient manner, for example, by means of hand dusters or sprayers or by simple mixing with the food to be ingested by the pests. Application to the foliage of plants is conveniently carried out with power dusters, boom sprayers, and fog sprayers. In such foliar applications, the employed composition should not contain any appreciable amounts of any phytotoxic diluents. In large scale operations, dust or low volume sprays can be applied from the air. The present invention also comprehends the employment of compositions comprising one or more of compounds of the present invention, an adjuvant, and one or more other biologically-active materials, such as other insecticides, fungicides, miticides, bactericides, nematacides, and the like.

It is usual in describing foliar applications of plant protectants to measure the application rate by the concentration of dispersion in which it is applied. The application rate is measured in this way because it is customary to apply a sufficient amount of the dispersion to cover the foliage with a thin film. The amount of dispersion applied is thus dependent on the foliar area of the plant, and the quantity of plant protecting compound is dependent upon its concentration in the dispersion.

Thus, the insecticidal method is carried out by applying the compound to the foliage of plants or other source of food for the insect, and applications are made in the same manner as already described. The insecticidal application rates are from about 10 ppm to about 2000 ppm. It is, of course, apparent that higher or lower concentrations can be employed, depending upon the insect species to be controlled, the plant or other food source to which application is to be made, and the potency or toxicity of the particular compound in the composition.

The activity of representative compounds of the present invention against Mexican bean beetle is illustrated by the following example.

EXAMPLE 54

The compounds to be tested were dissolved or suspended in 50:50 acetone:ethanol, and a blend of anionic and nonionic surfactants was added. The solution then was dispersed in water, so that the final dispersion contained about 20% of solvent and the concentration of test compounds shown in the table below.

The test compound dispersions were sprayed on the foliage of young bean plants in an amount sufficient to wet the foliage completely. The dispersions then were allowed to dry, and individual leaves were removed from the plants. The petiole of each leaf was wrapped in water-soaked cotton and the leaf then was infested with second instar larvae of Mexican bean beetle. Five larvae were applied to each leaf, and two replicates were used for each compound concentration. Mortality was observed on the fourth and seventh days after treatment.

Untreated control insects were included with every group of test insects.

Insect mortality produced by the compound was rated on a scale where 0 represented no mortality, 1 represented less than 50 percent mortality, 2 represented 51-99 percent mortality, and 3 represented 100 percent mortality of insects. Results were averaged where a compound was tested repeatedly against the insect. Empty spaces in the table indicate that the compound was not tested at the indicated rate. The results produced by typical compounds of the invention are summarized in the table which follows.

TABLE 1

| ACTIVITY OF REPRESENTATIVE COMPOUNDS AGAINST MEXICAN BEAN BEETLE | | | | | | | | | |
|---|---|---|---|---|---|---|---|---|---|
| | ORIGINAL TEST | | | | RETEST | | | | |
| Compound of | 1000 ppm. | | 100 ppm. | | 100 ppm. | 50 ppm. | 25 ppm. | 10 ppm. | 5 ppm. |
| Example | 4 days | 7 days | 4 days | 7 days | 7 days | 7 days | 7 days | 7 days | 7 days |
| 1 | | 3 | | 1 | | | | | |
| 2 | 3 | 3 | 2 | 3 | 3 | 3 | 2 | 1 | |
| 3 | 3 | 3 | 2 | 3 | 3 | 3 | 2 | | |
| 4 | 2 | 3 | 1 | 2 | 3 | 2 | 1 | 1 | |
| 5 | 3 | 3 | 3 | 3 | 3 | | | 1 | |
| 6 | 3 | 3 | 2 | 2 | 3 | 3 | 2 | 2 | 1 |
| 7 | 3 | 3 | 0 | 3 | 3 | 3 | 3 | 2 | 1 |
| 8 | 3 | 3 | 2 | 3 | 3 | 3 | 2 | | |
| 9 | 3 | 3 | 2 | 2 | 2 | | | | |
| 10 | 3 | 3 | 3 | 3 | 3 | 2 | 1 | | |
| 11 | 3 | 3 | 3 | 3 | 3 | | | | |
| 12 | | | 3 | 3 | 3 | 3 | 3 | 1 | |
| 13 | | | 2 | 3 | 3 | 3 | 2 | 1 | |
| 14 | | | 2 | 3 | 3 | 3 | 3 | 1 | |
| 15 | 2 | 3 | 2 | 3 | | | | | |
| 16 | 3 | 3 | 3 | 3 | 3 | 3 | 2 | 2 | |
| 17 | 3 | 3 | 1 | 2 | | | | | |
| 18 | 1 | 3 | | 3 | 3 | 3 | 3 | 2 | |
| 19 | 2 | 3 | | 3 | 3 | 3 | 2 | 1 | |
| 20 | 3 | 3 | 3 | 3 | 3 | 3 | 3 | 2 | |

TABLE 1-continued

| Compound of Example | ACTIVITY OF REPRESENTATIVE COMPOUNDS AGAINST MEXICAN BEAN BEETLE | | | | | | | | |
|---|---|---|---|---|---|---|---|---|---|
| | ORIGINAL TEST | | | | RETEST | | | | |
| | 1000 ppm. | | 100 ppm. | | 100 ppm. | 50 ppm. | 25 ppm. | 10 ppm. | 5 ppm. |
| | 4 days | 7 days | 4 days | 7 days | 7 days | 7 days | 7 days | 7 days | 7 days |
| 21 | 3 | 3 | 3 | 3 | 3 | 3 | 3 | 2 | |
| 22 | 3 | 3 | 2 | 3 | 3 | 3 | 3 | 1 | |
| 23 | 2 | 3 | 1 | 2 | | | | | |
| 24 | 2 | 3 | 1 | 3 | 3 | 3 | 3 | 2 | |
| 25 | 2 | 2 | 2 | 2 | 3 | 2 | 2 | 1 | |
| 26 | 3 | 3 | 2 | 3 | 3 | 3 | 3 | 1 | |
| 27 | 3 | 3 | 3 | 3 | 3 | 3 | 3 | 2 | 1 |
| 28 | 2 | 3 | 2 | 3 | 3 | 3 | 3 | 2 | |
| 29 | 3 | 3 | 3 | 3 | 3 | 3 | 3 | 2 | 1 |
| 30 | | 2 | | | | | | | |
| 31 | | | | 3 | | | | | |
| 32 | 2 | 3 | 2 | 3 | | | | | |
| 33 | 2 | 3 | 2 | 3 | 3 | 3 | 3 | 1 | |
| 34 | 3 | 3 | 3 | 3 | 3 | 3 | 2 | | |
| 35 | 2 | 3 | 1 | 3 | 3 | 3 | 3 | 2 | |
| 36 | 2 | 3 | | 1 | | | | | |
| 37 | 1 | 3 | | | | | | | |
| 38 | 3 | 3 | | 1 | | | | | |
| 39 | 2 | 3 | | 1 | | | | | |
| 40 | 3 | 3 | 1 | 3 | 3 | 3 | 2 | | |
| 41 | 3 | 3 | 3 | 3 | 3 | 2 | 2 | 1 | |
| 42 | 2 | 3 | 2 | 3 | 3 | 3 | 3 | 2 | |
| 43 | 3 | 3 | 1 | 2 | | | | | |
| 44 | 2 | 3 | 1 | 2 | | | | | |
| 45 | 3 | 3 | 3 | 3 | 3 | | | 1 | |
| 46 | 3 | 3 | 2 | 3 | 2 | 2 | 1 | | |
| 47 | 2 | 3 | 2 | 3 | 3 | 3 | 3 | 1 | |
| 48 | | | 3 | 3 | 3 | 3 | 3 | 1 | |
| 49 | 3 | 3 | 3 | 3 | 3 | 3 | 2 | 1 | |
| 50 | 3 | 3 | 3 | 3 | 3 | 3 | 3 | 2 | |
| 51 | 3 | 3 | 2 | 3 | 3 | 3 | 3 | | |
| 52 | 3 | 3 | 2 | 3 | 3 | 3 | 3 | | |
| 53 | 3 | 3 | 2 | 3 | 2 | 3 | 2 | 1 | |

What is claimed is:
1. A compound having the formula:

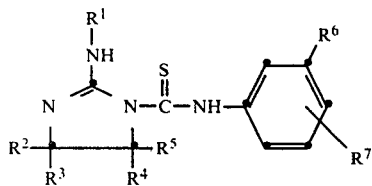

wherein R$^1$ represents
(A) C$_1$-C$_{18}$ alkyl;
(B) C$_2$-C$_{18}$ alkenyl;
(C) C$_4$-C$_{18}$ alkadienyl;
(D) C$_3$-C$_{12}$ cycloalkyl, optionally substituted with either one or two C$_1$-C$_3$ alkyl groups;
(E) C$_5$-C$_{12}$ cycloalkenyl, optionally substituted with either one or two C$_1$-C$_3$ alkyl groups;
(F) C$_6$-C$_{12}$ cycloalkadienyl, optionally substituted with either one or two C$_1$-C$_3$ alkyl groups;
(G) phenyl, optionally substituted with from one to three groups selected from the group consisting of
 (1) C$_1$-C$_6$ alkyl,
 (2) C$_1$-C$_6$ alkoxy,
 (3) C$_1$-C$_6$ alkylthio,
 (4) trifluoromethyl,
 (5) halo, and
 (6) cyano;
(H) (cycloalkyl)alkyl, containing no more than about 18 carbon atoms, in which the cycloalkyl moiety is as defined hereinabove;
(I) phenylalkyl, containing no more than about 18 carbon atoms, in which the phenyl moiety is as defined hereinabove;
(J) diphenylalkyl, containing no more than about 18 carbon atoms, in which each phenyl moiety is as defined hereinabove;
R$^2$ and R$^3$ independently are selected from the group consisting of
(A) hydrogen,
(B) C$_1$-C$_3$ alkyl, and
(C) phenyl, with the proviso that when one of R$^2$ and R$^3$ is phenyl, the other of R$^2$ and R$^3$ is hydrogen;
R$^4$ and R$^5$ independently are selected from the group consisting of
(A) hydrogen,
(B) C$_1$-C$_3$ alkyl, and
(C) phenyl, with the proviso that when one of R$^4$ and R$^5$ is phenyl, the other of R$^4$ and R$^5$ is hydrogen;
R$^6$ represents
(A) halo,
(B) trifluoromethyl,
(C) cyano, or
(D) 1,1,2,2-tetrafluoroethoxy;
R$^7$ represents hydrogen, C$_1$-C$_3$ alkyl, or halo, with the proviso that R$^7$ cannot be in the 2-position.

2. A compound of claim 1, wherein R$^1$ is selected from the group consisting of C$_1$-C$_{18}$ alkyl; phenyl, optionally monosubstituted with C$_1$-C$_3$ alkyl, C$_1$-C$_3$ alkoxy, trifluoromethyl, or halo, or optionally disubstituted with halo; and phenylalkyl, in which the phenyl moiety is unsubstituted.

3. A compound of claim 1, wherein R$^1$ is selected from the group consisting of C$_1$-C$_6$ alkyl; phenyl, optionally monosubstituted with fluoro, chloro, or bromo, or optionally disubstituted with chloro; and $C_7$–$C_{10}$ phenylalkyl, in which the phenyl moiety is unsubstituted.

4. A compound of claim 1, wherein each of $R^2$, $R^3$, $R^4$, and $R^5$ is hydrogen.

5. A compound of claim 1, wherein $R^6$ is selected from the group consisting of chloro, bromo, trifluoromethyl, and cyano.

6. A compound of claim 1, wherein $R^6$ is either chloro or bromo.

7. A compound of claim 1, wherein $R^7$ is hydrogen.

8. The compound of claim 1, which compound is N-(3-chlorophenyl)-2-propylamino-2-imidazoline-1-carbothioamide.

9. The compound of claim 1, which compound is N-(3-chlorophenyl)-2-phenylamino-2-imidazoline-1-carbothioamide.

10. The compound of claim 1, which compound is N-(3-bromophenyl)-2-phenylamino-2-imidazoline-1-carbothioamide.

11. The compound of claim 1, which compound is N-(3-iodophenyl)-2-phenylamino-2-imidazoline-1-carbothioamide.

12. The compound of claim 1, which compound is N-(3-cyanophenyl)-2-phenylamino-2-imidazoline-1-carbothioamide.

13. The compound of claim 1, which compound is N-(3-chlorophenyl)-2-(o-tolylamino)-2-imidazoline-1-carbothioamide.

14. The compound of claim 1, which compound is N-(3-chlorophenyl)-2-(m-tolylamino)-2-imidazoline-1-carbothioamide.

15. The compound of claim 1, which compound is N-(3-chlorophenyl)-2-(p-tolylamino)-2-imidazoline-1-carbothioamide.

16. The compound of claim 1, which compound is N-(3-chlorophenyl)-2-(4-ethylphenylamino)-2-imidazoline-1-carbothioamide.

17. The compound of claim 1, which compound is N-(3-chlorophenyl)-2-(3-trifluoromethylphenylamino)-2-imidazoline-1-carbothioamide.

18. The compound of claim 1, which compound is N-(3-chlorophenyl)-2-(2-fluorophenylamino)-2-imidazoline-1-carbothioamide.

19. The compound of claim 1, which compound is N-(3-chlorophenyl)-2-(3-fluorophenylamino)-2-imidazoline-1-carbothioamide.

20. The compound of claim 1, which compound is N-(3-chlorophenyl)-2-(2-chlorophenylamino)-2-imidazoline-1-carbothioamide.

21. The compound of claim 1, which compound is N-(3-chlorophenyl)-2-(3-chlorophenylamino)-2-imidazoline-1-carbothioamide.

22. The compound of claim 1, which compound is N-(3-bromophenyl)-2-(3-chlorophenylamino)-2-imidazoline-1-carbothioamide.

23. The compound of claim 1, which compound is N-(3-chlorophenyl)-2-(4-chlorophenylamino)-2-imidazoline-1-carbothioamide.

24. The compound of claim 1, which compound is 2-(4-bromophenylamino)-N-(3-chlorophenyl)-2-imidazoline-1-carbothioamide.

25. The compound of claim 1, which compound is N-(3-chlorophenyl)-2-(2,4-dichlorophenylamino)-2-imidazoline-1-carbothioamide.

26. The compound of claim 1, which compound is N-(3-chlorophenyl)-2-(3,4-dichlorophenylamino)-2-imidazoline-1-carbothioamide.

27. The compound of claim 1, which compound is 2-benzylamino-N-(3-fluorophenyl)-2-imidazoline-1-carbothioamide.

28. The compound of claim 1, which compound is N-(3-chlorophenyl)-2-phenethylamino-2-imidazoline-1-carbothioamide.

29. The compound of claim 1, which compound is N-(3-chlorophenyl)-2-(3-phenylpropylamino)-2-imidazoline-1-carbothioamide.

30. A method for reducing or eradicating a population of the insect species *Epilachna varivestis* which comprises administering to the insect by ingestion an insecticidally-effective amount of a compound of claim 1.

31. A method of claim 30, wherein $R^1$ is selected from the group consisting of alkyl; phenyl, optionally monosubstituted with $C_1$–$C_3$ alkyl, $C_1$–$C_3$ alkoxy, trifluoromethyl, or halo, or optionally disubstituted with halo; and phenylalkyl, in which the phenyl moiety is unsubstituted.

32. A method of claim 30, wherein $R^1$ is selected from the group consisting of $C_1$–$C_6$ alkyl; phenyl, optionally monosubstituted with fluoro, chloro, or bromo, or optionally disubstituted with chloro; and $C_7$–$C_{10}$ phenylalkyl, in which the phenyl moiety is unsubstituted.

33. A method of claim 30, wherein each of $R^2$, $R^3$, $R^4$, and $R^5$ are hydrogen.

34. A method of claim 30, wherein $R^6$ is selected from the group consisting of chloro, bromo, trifluoromethyl, and cyano.

35. A method of claim 30, wherein $R^6$ is either chloro or bromo.

36. A method of claim 31, wherein $R^7$ is hydrogen.

37. The method of claim 30, in which the compound is N-(3-chlorophenyl)-2-propylamino-2-imidazoline-1-carbothioamide.

38. The method of claim 30, in which the compound is N-(3-fluorophenyl)-2-phenylamino-2-imidazoline-1-carbothioamide.

39. The method of claim 30, in which the compound is N-(3-chlorophenyl)-2-phenylamino-2-imidazoline-1-carbothioamide.

40. The method of claim 30, in which the compound is N-(3-bromophenyl)-2-phenylamino-2-imidazoline-1-carbothioamide.

41. The method of claim 30, in which the compound is N-(3-iodophenyl)-2-phenylamino-2-imidazoline-1-carbothioamide.

42. The method of claim 30, in which the compound is N-(3-cyanophenyl)-2-phenylamino-2-imidazoline-1-carbothioamide.

43. The method of claim 30, in which the compound is N-(3-chlorophenyl)-2-(o-tolylamino)-2-imidazoline-1-carbothioamide.

44. The method of claim 30, in which the compound is N-(3-chlorophenyl)-2-(m-tolylamino)-2-imidazoline-1-carbothioamide.

45. The method of claim 30, in which the compound is N-(3-chlorophenyl)-2-(p-tolylamino)-2-imidazoline-1-carbothioamide.

46. The method of claim 30, in which the compound is N-(3-chlorophenyl)-2-(4-ethylphenylamino)-2-imidazoline-1-carbothioamide.

47. The method of claim 30, in which the compound is N-(3-chlorophenyl)-2-(3-trifluoromethylphenylamino)-2-imidazoline-1-carbothioamide.

48. The method of claim 30, in which the compound is N-(3-chlorophenyl)-2-(2-fluorophenylamino)-2-imidazoline-1-carbothioamide.

49. The method of claim 30, in which the compound is N-(3-chlorophenyl)-2-(3-fluorophenylamino)-2-imidazoline-1-carbothioamide.

50. The method of claim 30, in which the compound is N-(3-chlorophenyl)-2-(2-chlorophenylamino)-2-imidazoline-1-carbothioamide.

51. The method of claim 30, in which the compound is N-(3-chlorophenyl)-2-(3-chlorophenylamino)-2-imidazoline-1-carbothioamide.

52. The method of claim 30, in which the compound is N-(3-bromophenyl)-2-(3-chlorophenylamino)-2-imidazoline-1-carbothioamide.

53. The method of claim 30, in which the compound is N-(3-chlorophenyl)-2-(4-chlorophenylamino)-2-imidazoline-1-carbothioamide.

54. The method of claim 30, in which the compound is 2-(4-bromophenylamino)-N-(3-chlorophenyl)-2-imidazoline-1-carbothioamide.

55. The method of claim 30, in which the compound is N-(3-chlorophenyl)-2-(2,4-dichlorophenylamino)-2-imidazoline-1-carbothioamide.

56. The method of claim 30, in which the compound is N-(3-chlorophenyl)-2-(3,4-dichlorophenylamino)-2-imidazoline-1-carbothioamide.

57. The method of claim 30, in which the compound is 2-benzylamino-N-(3-fluorophenyl)-2-imidazoline-1-carbothioamide.

58. The method of claim 30, in which the compound is N-(3-chlorophenyl)-2-phenethylamino-2-imidazoline-1-carbothioamide.

59. The method of claim 30, in which the compound is N-(3-chlorophenyl)-2-(3-phenylpropylamino)-2-imidazoline-1-carbothioamide.

60. An insecticidal composition which comprises an insecticidally-effective amount of a compound of claim 1 and an agriculturally-acceptable carrier.

61. A composition of claim 60, wherein $R^1$ is selected from the group consisting of alkyl; phenyl, optionally monosubstituted with $C_1$-$C_3$ alkyl, $C_1$-$C_3$ alkoxy, trifluoromethyl, or halo, or optionally disubstituted with halo; and phenylalkyl, in which the phenyl moiety is unsubstituted.

62. A composition of claim 60, wherein $R^1$ is selected from the group consisting of $C_1$-$C_6$ alkyl; phenyl, optionally monosubstituted with fluoro, chloro, or bromo, or optionally disubstituted with chloro; and $C_7$-$C_{10}$ phenylalkyl, in which the phenyl moiety is unsubstituted.

63. A composition of claim 60, wherein each of $R^2$, $R^3$, $R^4$, and $R^5$ are hydrogen.

64. A composition of claim 60, wherein $R^6$ is selected from the group consisting of chloro, bromo, trifluoromethyl, and cyano.

65. A composition of claim 60, wherein $R^6$ is either chloro or bromo.

66. A composition of claim 60, wherein $R^7$ is hydrogen.

67. The composition of claim 60, in which the compound is N-(3-chlorophenyl)-2-propylamino-2-imidazoline-1-carbothioamide.

68. The composition of claim 60, in which the compound is N-(3-fluorophenyl)-2-phenylamino-2-imidazoline-1-carbothioamide.

69. The composition of claim 60, in which the compound is N-(3-chlorophenyl)-2-phenylamino-2-imidazoline-1-carbothioamide.

70. The composition of claim 60, in which the compound is N-(3-bromophenyl)-2-phenylamino-2-imidazoline-1-carbothioamide.

71. The composition of claim 60, in which the compound is N-(3-iodophenyl)-2-phenylamino-2-imidazoline-1-carbothioamide.

72. The composition of claim 60, in which the compound is N-(3-cyanophenyl)-2-phenylamino-2-imidazoline-1-carbothioamide.

73. The composition of claim 60, in which the compound is N-(3-chlorophenyl)-2-(o-tolylamino)-2-imidazoline-1-carbothioamide.

74. The composition of claim 60, in which the compound is N-(3-chlorophenyl)-2-(m-tolylamino)-2-imidazoline-1-carbothioamide.

75. The composition of claim 60, in which the compound is N-(3-chlorophenyl)-2-(p-tolylamino)-2-imidazoline-1-carbothioamide.

76. The composition of claim 60, in which the compound is N-(3-chlorophenyl)-2-(4-ethylphenylamino)-2-imidazoline-1-carbothioamide.

77. The composition of claim 60, in which the compound is N-(3-chlorophenyl)-2-(3-trifluoromethylphenylamino)-2-imidazoline-1-carbothioamide.

78. The composition of claim 60, in which the compound is N-(3-chlorophenyl)-2-(2-fluorophenylamino)-2-imidazoline-1-carbothioamide.

79. The composition of claim 60, in which the compound is N-(3-chlorophenyl)-2-(3-fluorophenylamino)-2-imidazoline-1-carbothioamide.

80. The composition of claim 60, in which the compound is N-(3-chlorophenyl)-2-(2-chlorophenylamino)-2-imidazoline-1-carbothioamide.

81. The composition of claim 60, in which the compound is N-(3-chlorophenyl)-2-(3-chlorophenylamino)-2-imidazoline-1-carbothioamide.

82. The composition of claim 60, in which the compound is N-(3-bromophenyl)-2-(3-chlorophenylamino)-2-imidazoline-1-carbothioamide.

83. The composition of claim 60, in which the compound is N-(3-chlorophenyl)-2-(4-chlorophenylamino)-2-imidazoline-1-carbothioamide.

84. The composition of claim 60, in which the compound is 2-(4-bromophenylamino)-N-(3-chlorophenyl)-2-imidazoline-1-carbothioamide.

85. The composition of claim 60, in which the compound is N-(3-chlorophenyl)-2-(2,4-dichlorophenylamino)-2-imidazoline-1-carbothioamide.

86. The composition of claim 60, in which the compound is N-(3-chlorophenyl)-2-(3,4-dichlorophenylamino)-2-imidazoline-1-carbothioamide.

87. The composition of claim 60, in which the compound is 2-benzylamino-N-(3-fluorophenyl)-2-imidazoline-1-carbothioamide.

88. The composition of claim 60, in which the compound is N-(3-chlorophenyl)-2-phenethylamino-2-imidazoline-1-carbothioamide.

89. The composition of claim 60, in which the compound is N-(3-chlorophenyl)-2-(3-phenylpropylamino)-2-imidazoline-1-carbothioamide.

* * * * *